United States Patent [19]

Shaw

[11] Patent Number: 5,922,689
[45] Date of Patent: Jul. 13, 1999

[54] CISPLATIN ANALOGS FOR CANCER TREATMENT

[75] Inventor: Jiajiu Shaw, Ann Harbor, Mich.

[73] Assignee: Unitech Pharmaceuticals, Inc., Ann Arbor, Mich.

[21] Appl. No.: 08/818,444

[22] Filed: Mar. 17, 1997

Related U.S. Application Data

[63] Continuation of application No. 08/526,760, Sep. 11, 1995, abandoned.

[51] Int. Cl.$^6$ .......................... A61K 31/28; A61K 31/70; A61K 33/24
[52] U.S. Cl. ............................ 514/45; 514/46; 514/492; 536/22.1; 536/27.81; 424/489; 556/136
[58] Field of Search ................. 536/27.81, 22.1; 424/489; 514/492, 19, 45, 46; 556/136

[56] References Cited

U.S. PATENT DOCUMENTS

| | | | |
|---|---|---|---|
| 4,140,707 | 2/1979 | Cleare et al. | 260/429 R |
| 4,207,416 | 6/1980 | Hoeschele | 536/28.53 |
| 4,760,157 | 7/1988 | Child et al. | 556/137 |
| 4,808,730 | 2/1989 | Bitha et al. | 549/211 |
| 4,937,358 | 6/1990 | Bitha et al. | 549/206 |
| 4,996,337 | 2/1991 | Bitha et al. | 556/137 |

OTHER PUBLICATIONS

Biochemistry, vol. 24, pp. 707–713 (1985).
Peresie et al., Inorganica Chimica Acta, vol. 29, pp. L247–L248 (1978).
Miller et al., Inorg. Chem., vol. 24, pp. 2421–2425, (1985).
Hollis et al., Chemical and Biological Properties of a New Series of cis–Diammineplatinum(II) Antitumor Agents Containing Three Nitrogen Donors: cis–$[Pt(NH_3)_2(N-donor)Cl]^+$, J. Med. Chem. 1989, 32, 128–136.

*Primary Examiner*—James O. Wilson
*Attorney, Agent, or Firm*—Brinks Hofer Gilson & Lione

[57] ABSTRACT

This invention comprises the synthesis and the use of two cisplatin analogs $[Pt(NH_3)_2Cl(C_{10}H_{13}N_5O_5)]Cl$ and $[Pt(NH_3)_2(C_{10}H_{13}N_5O_5)_2]Cl_2$, whereby $(C_{10}H_{13}N_5O_5)$ is guanosine. The stoichiometric ratio between cisplatin and guanosine may be 1:1 or 1:2. The complexes are to be used in cancer treatment, they may also be used to treat AIDS patients.

7 Claims, 4 Drawing Sheets

5,922,689

CISPLATIN ANALOGS FOR CANCER TREATMENT

This application is a continuation of application Ser. No: 08/526,760, Filed: Sep. 11, 1995, which is abandoned.

FIELD OF INVENTION

This invention relates to two complexes formed by cisplatin and guanosine, specifically the synthesis and the use of these two complexes.

1. Background
2. Prior Art

Cisplatin (cis-diamminedichloroplatinum, cis-Pt(NH$_3$)$_2$Cl$_2$, molecular weight 300.05) has been used as a chemotherapeutic agent for many years since the discovery of its anti-tumor activity by B. Rosenberg et. al. (*Nature*, 1965, 205, 698, *Nature*, 1972, 222, 385).

After so many years, cisplatin is still being widely used because of its efficacy. However, its major drawback, the toxicity, is still a big concern.

Many attempts have been made to modify cisplatin in order to reduce its toxicity, many attempts have also been made to understand the interaction between cisplatin and DNA which is the ultimate target of cisplatin.

In terms of modifying the cisplatin molecule, many people have attempted to change the ligand on Platinum. Examples are made by K. C. Tsou, et al. (*J. Clin. Hemat. Oncol.* 1977, 7, 322,), R. J. Speeder et al. (*J. Clin. Hemat. Oncol.* 1977, 7, 210), A. Mathew et. al. (*Chem. Comm.* 1979, 222), D. Rose, et al. (*Cancer Treatment Reviews*, 1985, 12, 1), and D. Alberts et al. (*Cancer Treatment Reviews*, 1985, 12, 83).

In terms of understanding the interaction between cisplatin and DNA, the X-ray structure of the adduct of cisplatin and DNA was determined by S. E. Sherman et al. (*Science* 1985, 230, 412). This critical work provides a very clear insight as to how cisplatin may function as an inhibitor to stop the DNA replication process, thus, kill the cell eventually. Their studies show that cisplatin binds to synthetic oligodeoxynucleotides to form cis-[Pt(NH$_3$)$_2${d(pGpG)}], where "d(pGpG)" represents dinucleotide made of deoxyguanosine monophosphate. They indicated that the intrastrand cross-linked cis-[Pt(NH$_3$)$_2${d(pGpG)}] is a very possible reason why cisplatin is capable of inhibiting DNA replication. Fichtinger-Schepman et. al., (Biochemistry, 1985, 24, 707–713) synthesized and identified four adducts of cisplatin and DNA residues. They are: cis-[Pt(NH$_3$)$_2$d(pGpG)], cis-[Pt(NH$_3$)$_2$d(pApG)], cis-[Pt(NH$_3$)$_3$dGMP], cis-[Pt(NH$_3$)$_2$(dGMP)$_2$], where "d(pGpG)" represents dinucleotide made of deoxyguanosine monophosphate, "d(pApG)" represents dinucleotide made of deoxyadenosine monophosphate and deoxyguanosine monophosphate, and dGMP represents deoxyguanosine monophosphate.

The most common binding of cisplatin to DNA is through the loss of chloride ion to form Pt-N bond to the N$_7$ of guanine. All known references indicate that N$_7$ of guanine is the major binding site for guanosine nucleotide. Examples of the references are F. J. Dijt et al. (*J. Am. Chem. Soc.* 1984, 106, 3644–3647), A. M. J. Fichtinger-Schepman et al. (*Biochemistry* 1985, 24, 707–713), and S. E. Sherman et al. (*Science* 1985, 230, 412–417).

In an effort to make different cisplatin analogs, this invention uses Sherman's finding as a basis to synthesize the cisplatin analogs. This invention comprises the two complexes made from cisplatin and guanosine. One complex is made by the reaction between cisplatin and guanosine at the mole ratio of 1:1, another complex may be made at the mole ration of 1:2 in a similar manner.

Because these two cisplatin analogs are also guanosine analogs, these new compounds may have stronger affinity to the DNA or RNA being replicated. Very likely, the guanosine residue of the new compounds may be incorporated in DNA or RNA during the replication process, thus, incorporating the pre-existing Pt-guanosine binding in the replication process of DNA or RNA and achieve the goal of killing cancer cells.

Based on the studies of R. A. Lerner et al. (*Proc. Natl. Acad. Sci. USA*, 1971, 68, 1212), J. C. Rogers et al. (*J. Immuno.* 1981, 126, 703), J. Woo et al (*Biochem. J.* 1972, 128, 1273), and D. A. Juckett et al (*Cancer Research* 1982, 42, 3565), it was shown that most cancer cells have DNA or RNA sticking out of the cell. It is conceivable that a drug molecule comprising available nucleoside may be more likely to be grabbed by the DNA or RNA sticking on the outside of the cancer cells, thus, giving the drug molecule better opportunity to attack the cancer cells. As a result, the drug may be less toxic.

SUMMARY OF THE INVENTION

The objectives of this invention are as follow:

BRIEF DESCRIPTION OF THE DRAWINGS

FIG. 1(*b*) is a mass spectrum of a 1:1 cisplatin:guanosine adduct in glycerol matrix.

FIG. 2(*b*) is a mass spectrum of a 1:1 cisplatin:guanosine adduct in nitrobenzyl alcohol matrix.

Figure 1A:
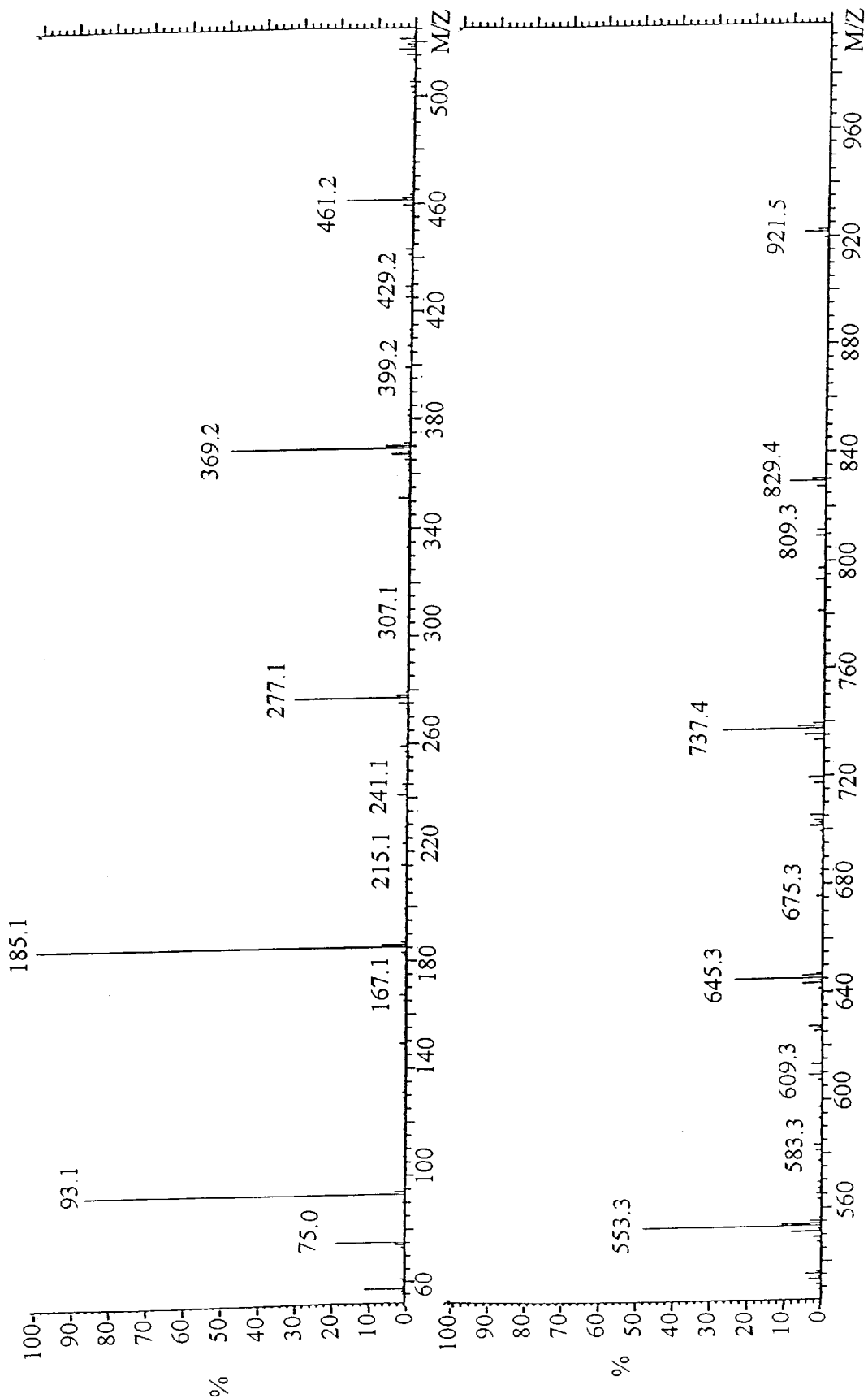
FIG. 1(*a*) is a mass spectrum of a matrix of glycerol.

1. To synthesize platinum complexes for cancer treatment

These two complexes made by cisplatin and guanosine have very good potential to be used as anti-cancer agents based on the characteristics of cisplatin and guanosine, the related studies from the references mentioned in the Background-Prior Art section, as well as the in-vitro results presented in this invention.

2. To modify cisplatin to make it less toxic or more efficacious

Because of the addition of guanosine residue onto cisplatin, these cisplatin analogs are actually guanosine analogs, too. These new complexes may have stronger affinity to the DNA or RNA being replicated outside of cancer cells because guanosine is a constitute of DNA or RNA main frame. This means they have weaker affinity to normal cells, thus, less toxic to normal cells.

3. To make new complexes which have good potential for treating Acquired Immune Deficiency Syndrome (AIDS)

Because the two complexes are likely to act on DNA or RNA of viruses, such as Human Immunodeficiency Virus (HIV), the compounds have very good potential to be used in AIDS treatment. These complexes may also be used in combination with other AIDS drugs, such as 3'-azidothymidine (AZT), to interfere with the HIV enzyme reverse transcriptase and achieve the goal of hampering the reproduction of HIV.

DETAILED DESCRIPTION OF THE INVENTION

This invention comprises two complexes made by cisplatin and guanosine at 1:1 and 1:2 stoichiometric ratios. The name of the 1:1 complex, cis-[Pt(NH$_3$)$_2$Cl(C$_{10}$H$_{13}$N$_5$O$_5$)]Cl, is tentatively given as "cis-diamminechloroguanosineplatinum chloride", its molecular weight is 583.29. The 1:2 complex, cis-$[Pt(NH_3)_2(C_{10}H_{13}N_5O_5)_2]Cl_2$, is tentatively named as "cis-diamminediguanosineplatinum chloride", its molecular weight is 866.53. Like many other compounds, they may contain small amount of solvent in which the synthesis or purification is processed.

These two complexes may be made in water or in a mixture of water and methanol. Specific examples of making these two compounds are as follow:

[EXAMPLE 1]

Specific example of making cis-$[Pt(NH_3)_2Cl(Guanosine)]Cl$

1. Accurately weigh about 100 mg of cisplatin and stir in about 50 mL of methanol using a magnetic stirrer; gradually add ca. 200 mL of water to aid the dissolution of cisplatin. This is aliquot A.
2. Accurately weigh about 95 mg of guanosine (on the dry basis) and suspend it about 100 mL of water by mixing with a magnetic stirrer. This is aliquot B.
3. Pour aliquot B into aliquot A, mix overnight by a magnetic stirrer until all materials are dissolved. This is solution C.
4. Carefully and slowly concentrate solution C under vacuum, until dry. Slowly add no more than 60 mL of water until most of the solid is dissolved. Filter off the precipitate and collect the filtrate. This filtrate is solution D.
5. Concentrate and dry solution D under vacuum. This makes light yellow powder E.
6. Wash the light yellow powder E with no more than 5 mL of ice water; filter and dry the powder again to obtain the final product, cis-$[Pt(NH_3)_2Cl(Guanosine)]Cl$. The final product may contain small amount of solvent.

[EXAMPLE 2]

Analytical results for cis-$[Pt(NH_3)_2Cl(Guanosine)]Cl$ made in Example 1

The complex from [Example 1] decomposes into black material at 214° C. indicating that it is a pure compound different from cisplatin (decomposed at 270° C.) and guanosine (decomposed at 240° C.).

The solubility of this complex in water at ambient temperature is 2.6 mg/mL. C,H,N elemental analysis was performed by National Chemical Consulting in Tenafly, N.J., and the results are as follow:

| | % C | % H | % N |
|---|---|---|---|
| Found (dried at 100° C. for 3 hours), first analysis: | 20.39 | 3.38 | 16.60 |
| Found (dried at 100° C. for 3 hours), second analysis: | 20.15 | 3.47 | 16.35 |
| average: | 20.27 | 3.43 | 16.48 |
| Theoretical: cis-$[Pt(NH_3)_2Cl(C_{10}H_{13}N_5O_5)]^+Cl^-$ | 20.27 | 3.26 | 16.80 |
| Theoretical: cis-$[Pt(NH_3)_2Cl(C_{10}H_{13}N_5O_5)]^+Cl^-$ with ½ $H_2O$ | 20.26 | 3.38 | 16.54 |
| Theoretical: cis-$[Pt(NH_3)_2Cl(C_{10}H_{13}N_5O_5)]^+Cl^-$ with 1 $H_2O$ | 19.96 | 3.49 | 16.30 |
| Theoretical: cis-$[Pt(NH_3)_2(H_2O)(C_{10}H_{13}N_5O_5)]^+Cl_2^-$ where $C_{10}H_{13}N_5O_5$ is guanosine. | 19.96 | 3.49 | 16.30 |

According to the above C,H,N elemental analysis data, the new compound appears to be cis-$[Pt(NH_3)_2Cl(Guanosine)]Cl$ associated with ½ $H_2O$. However, there is a slight chance that it might be cis-$[Pt(NH_3)_2(H_2O)(Guanosine)]Cl_2$ even though the data do not quite match.

Thus, additional analysis was considered to confirm that the complex is cis-$[Pt(NH_3)_2Cl(Guanosine)]Cl$. Due to the possible exchange of Cl and $H_2O$ in the solution, NMR may not be able to distinguish between cis-$[Pt(NH_3)_2Cl(C_{10}H_{13}N_5O_5)]Cl$ and cis-$[Pt(NH_3)_2(H_2O)(C_{10}H_{13}N_5O_5)]Cl_2$. Thus, mass spectrometry was performed.

Mass spectrometer was performed by the Mass Spectroscopy Laboratory of the University of Kansas, Lawrence, Kans., employing Fast Atom Bombardment (FAB).

Figure 1B:
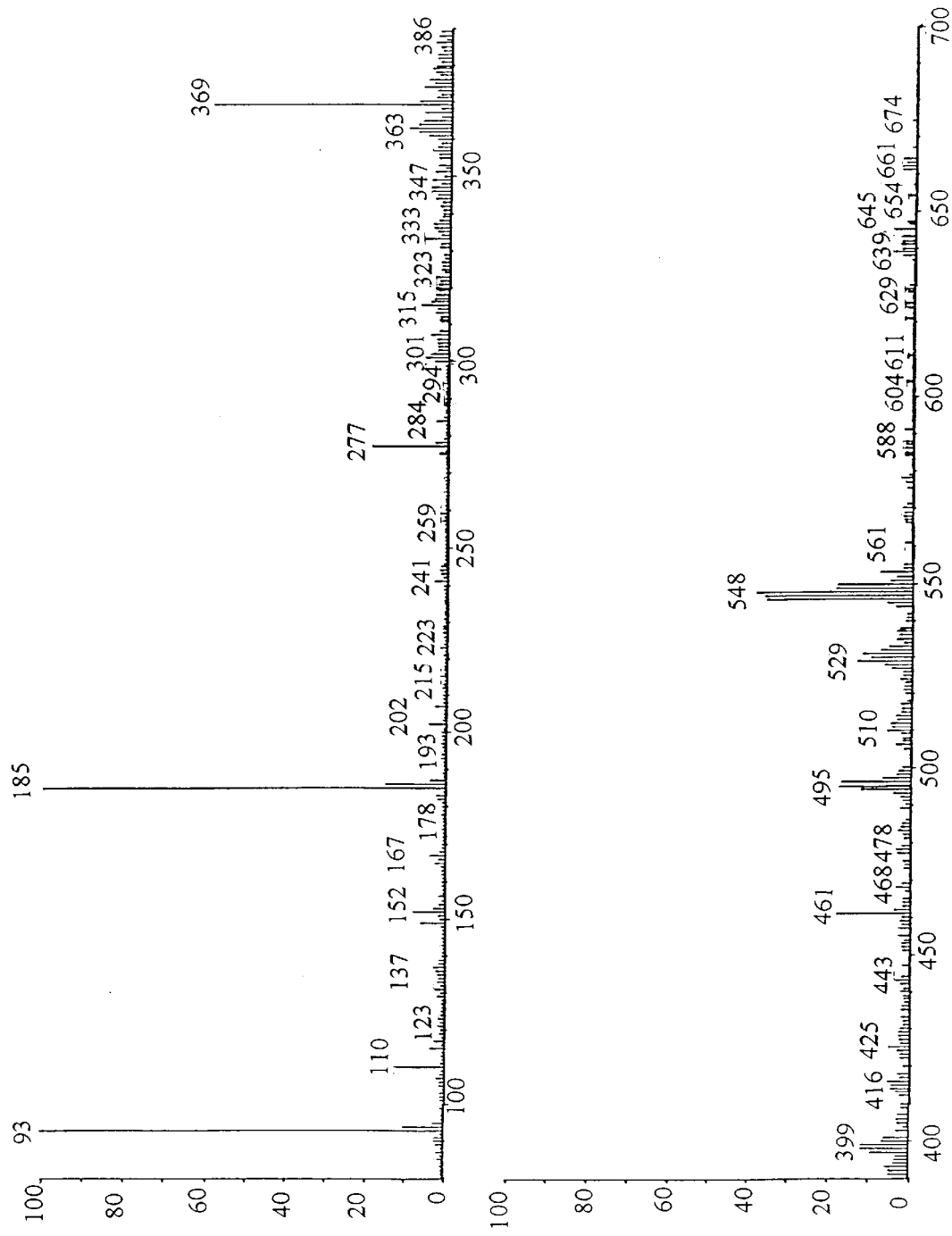

As shown in FIG. 1, when glycerol was used as the matrix, the major cluster of peaks were found at around 547; this is due to the many isotopes, Pt-190 (0.01%), Pt-192 (0.8%), Pt (194 (32.9%), Pt-195(33.8%), Pt-196 (25.2%), Pt-198 (7.2%). The three main peaks at this cluster are at 546, 547, and 548 which correspond to the cation fragment, cis-$[Pt(NH_3)_2Cl(C_{10}H_{13}N_5O_5)]^+$. This triplet at an approximate ratio of 1:1:1 is due to the isotopes, Pt-194 (32.9%), Pt-195 (33.8%), and Pt-196 (25.2%). Therefore, it confirms that the new compound synthesized is cis-$[Pt(NH_3)_2Cl(C_{10}H_{13}N_5O_5)]Cl$.

The other less intense peak clusters coming from smaller fragments in the order of decreasing intensity are found at [494, 495, 496], [529, 530, 531], [397, 398, 399], and [510, 511, 512]. These are weaker signals and may be use to support the main fragment. The cluster found at around 495 (547−17−35.5=494.5) matches the mass of fragment $Pt(NH_3)(C_{10}H_{13}N_5O_5)$ which is one "$NH_3$" and one "Cl" less than the main fragment. The cluster found at around 530 (547−17=530) matches the mass of $Pt(NH_3)Cl(C_{10}H_{13}N_5O_5)$ which is one "$NH_3$" less than the main fragment. The cluster found at around 399 (530−12×5−9−16×4=397) matches the mass of the $Pt(NH_3)Cl(C_{10}H_{13}N_5O_5)$ fragment less the ribose residue, "$C_5 H_9O_4$". The cluster at around 511 (547−35.5=511.5) matches the mass of "$Pt(NH_3)_2(C_{10}H_{13}N_5O_5)$" which is one "Cl" less than the main fragment.

If the new compound were cis-$[Pt(NH_3)_2(H_2O)(Guanosine)]Cl_2$, there should be a strong major cluster at around 530. However, the cluster at around 530 appears to be pretty weak indicating that it is a secondary fragment, $Pt(NH_3)Cl(C_{10}H_{13}N_5O_5)$, and not the main fragment.

Figure 2A:
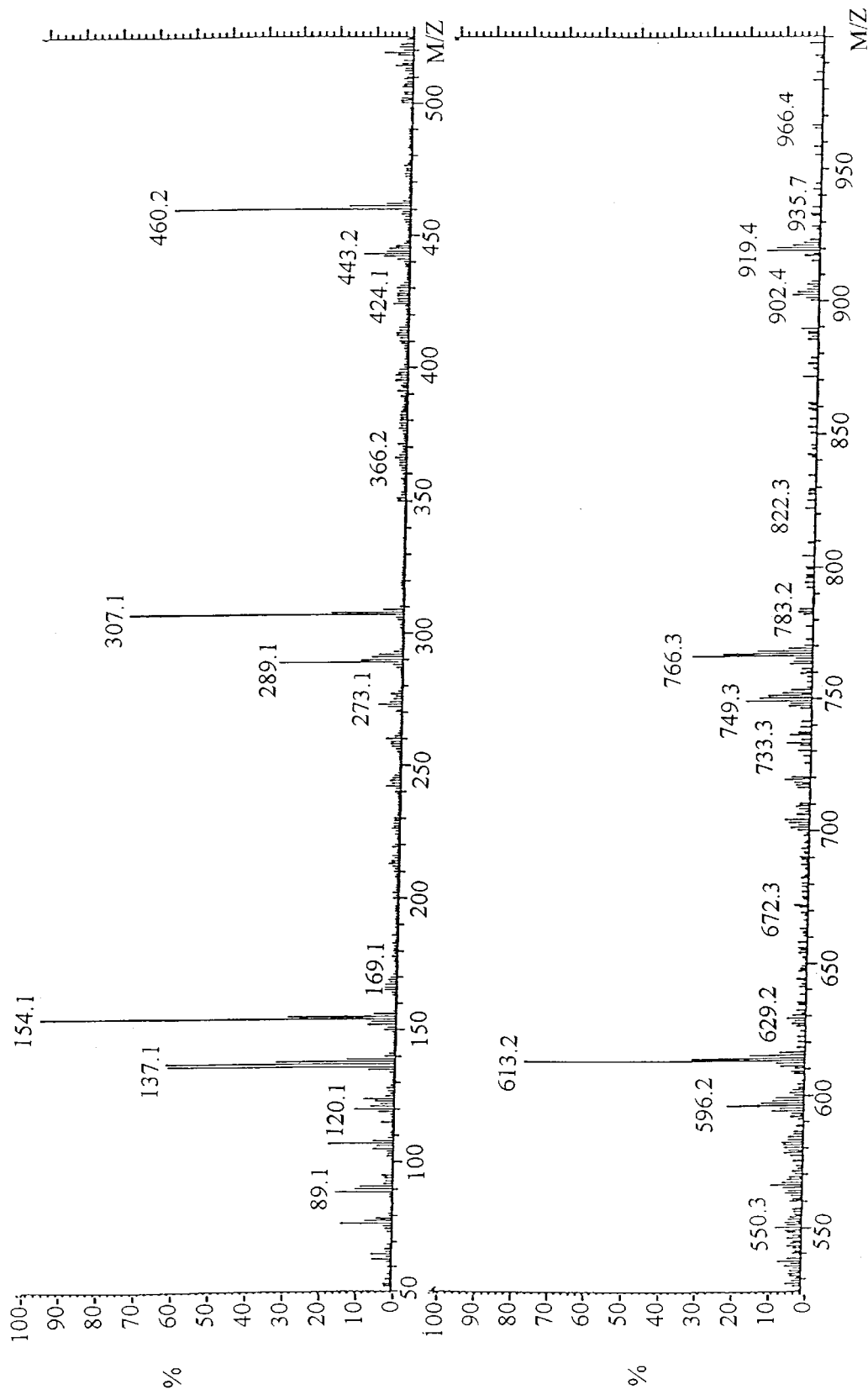
FIG. 2(*a*) is a mass spectrum of a matrix of nitrobenzyl alcohol.
Figure 2B:
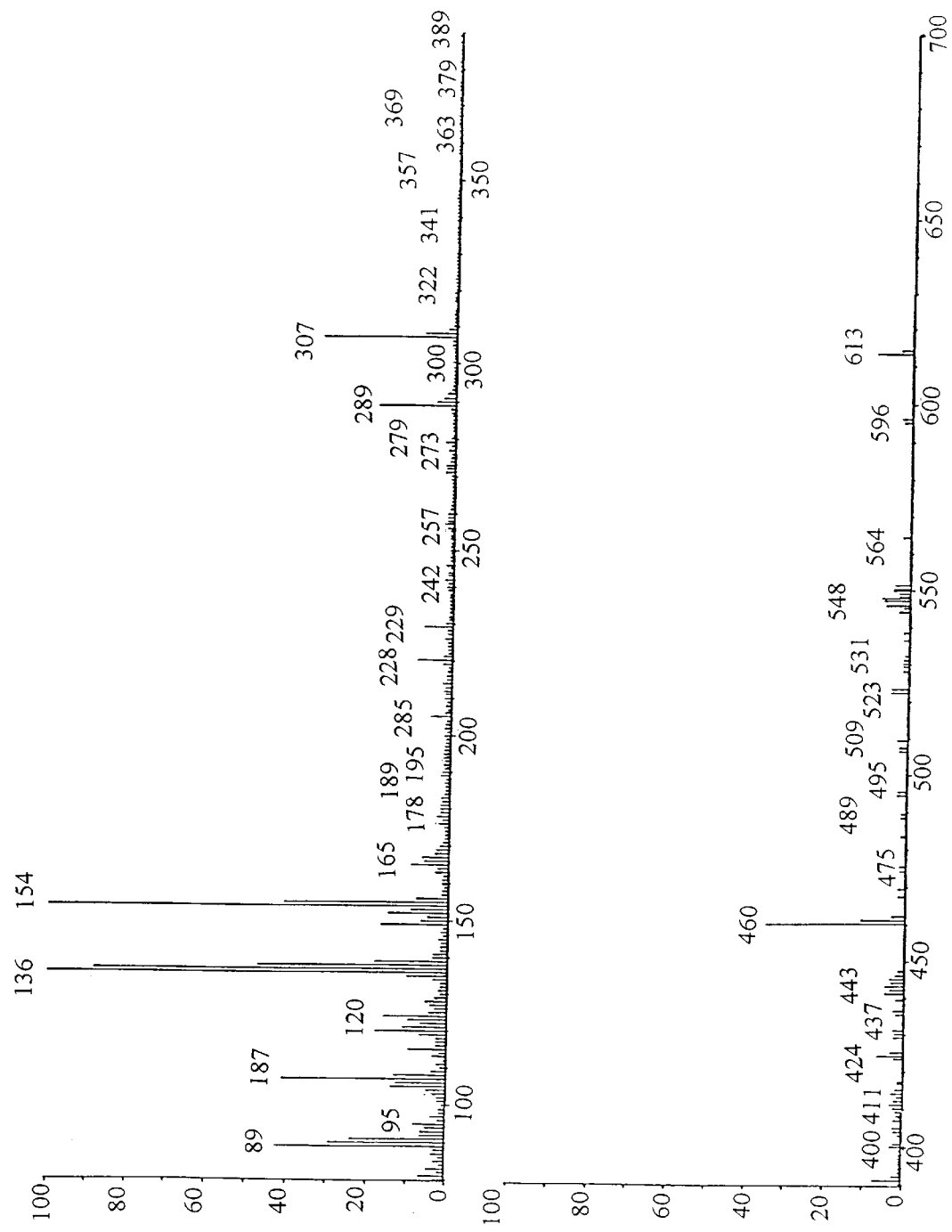

When nitrobenzyl alcohol was used as the matrix (FIG. 2), the only significant cluster of peaks observed was at around 548 confirming the main fragment, cis-$[Pt(NH_3)_2Cl(C_{10}H_{13}N_5O_5)]^+$.

The above results from mass spectroscopy further prove that the new compound is cis-$[Pt(NH_3)_2Cl(Guanosine)]^+Cl^-$ and not cis-$[Pt(NH_3)_2(H_2O)(Guanosine)]^+Cl^-_2$.

[EXAMPLE 3]

Another specific example of making cis-$[Pt(NH_3)_2Cl(Guanosine)]Cl$

1. Accurately weigh about 69 mg of cisplatin and 65 mg of guanosine (on the dry basis) into 70 mL of water; mix by a magnetic stirrer for no less than one day.
2. Filter off any solid and collect the filtrate.
3. Concentrate the filtrate under vacuum at 85–90° C. until it is almost dry (ca. 2–5 mL). Add 2–5 mL of cold water to help suspend the solid.
4. Filter and collect the solid (discard the filtrate).
5. Dry the solid to obtain the final product, cis-$[Pt(NH_3)_2(Guanosine)]Cl$.

[EXAMPLE 4]

Specific procedure for making cis-$[Pt(NH_3)_2(Guanosine)_2]Cl_2$

Use the same exact procedure as in Example 3, except the following modification:

"Use 130 mg of guanosine instead of 65 mg."

Due to the theory mentioned before, these two complexes (stoichiometric ratios of 1:1 and 1:2) may be used for cancer treatment and may have better efficacy and/or less toxicity. The following in-vitro results in [Examples 5] and [Example 6] further prove this rationale.

[EXAMPLE 5]

In-vitro inhibition of cancer cells by cis-[$(NH_3)_2$PtCl(Guanosine)]Cl (performed by Biotherapies Incorporated, Ann Arbor, Mich.)

Test solution: A solution of cis-diamminechloroguanosineplatinum chloride (cis-[Pt($NH_3$)$_2$Cl(Guanosine)]Cl, molecular weight 583.29) is diluted to 100 times final concentration in minimal essential media (MEM) and sterilized by passing through a 0.22 μm filter.

Growth Assay: plate individual cells (human breast cancer cells MCF-7, and MDA-MB-231) at $10^4$ cells/mL, 1-mL/well in MEM-10 (MEM+10% FBS, where FBS is fetal Bovine Serum) with 1/100 Penicillin/Strep. Add 1/100 volume of the above Test Solution (10 μL/mL) to triplicate wells. MCF-7 also requires 10 μg/mL insulin; MDA-MB-231 requires no insulin. Incubate cell cultures at 37° C. for 6 days and count the number of cells. The following results show that cis-[Pt($NH_3$)$_2$Cl(Guanosine)]Cl is able to inhibit the cell growth of MCF-7 and MDA-MB-231.

| Conc. (mg/mL) | Conc. (mmole/mL) | MCF-7 cell count | % inhibition |
|---|---|---|---|
| MCF-7 cell counts after treated by cis-[Pt($NH_3$)$_2$Cl(Guanosine)]Cl at different concentrations: | | | |
| 0 | 0 | $6.70 \times 10^5$ | 0 |
| 0.025 | $4.29 \times 10^{-5}$ | $1.00 \times 10^4$ | 98.5 |
| 0.0025 | $4.29 \times 10^{-6}$ | $5.00 \times 10^4$ | 92.5 |
| 0.00025 | $4.29 \times 10^{-7}$ | $6.10 \times 10^5$ | 9.0 |
| MDA cell counts after treated by cis-[Pt($NH_3$)$_2$Cl(Guanosine)]Cl at different concentrations: | | | |
| 0 | 0 | $4.00 \times 10^5$ | 0 |
| 0.025 | $4.29 \times 10^{-5}$ | $1.00 \times 10^4$ | 97.5 |
| 0.0025 | $4.29 \times 10^{-6}$ | $5.00 \times 10^4$ | 87.5 |
| 0.00025 | $4.29 \times 10^{-7}$ | $3.55 \times 10^5$ | 11.3 |

[EXAMPLE 6]

side-by-side comparison of cis-[Pt($NH_3$)$_2$PtCl(Guanosine)]Cl and cisplatin (performed by Biotherapies Incorporated of Ann Arbor, Mich.)

Test Solutions: Test solutions were prepared in the same manner as in Example 5, except, additional test solution was prepared employing cisplatin.

Growth Assay: The same method in Example 5 was used. However, the cells studied were normal human mammary cells and breast cancer cells, MCF-7. The following results indicate that at the concentration of ca. 8×10-5 mmole/mL cis-[Pt($NH_3$)$_2$Cl(Guanosine)]Cl is as effective as cisplatin in killing MCF-7 cells, yet, its toxicity to normal human mammary cells is lower than cisplatin.

| Conc. (mg/mL) | Conc. (mmole/mL) | MCF-7 cell count | % inhibition |
|---|---|---|---|
| For MCF-7 breast cancer cells | | | |
| 0 | 0 | $2.96 \times 10^6$ | 0 |
| #95001, 0.05 | $8.57 \times 10^{-5}$ | $6.70 \times 10^3$ | 99.8 |
| cisplatin, 0.025 | $8.33 \times 10^{-5}$ | $5.00 \times 10^3$ | 99.9 |
| #95001, 0.025 | $4.29 \times 10^{-5}$ | $3.30 \times 10^3$ | 97.6 |
| cisplatin, 0.012 | $4.00 \times 10^{-5}$ | $5.00 \times 10^3$ | 99.8 |
| For normal human mammary cells | | | |
| 0 | 0 | $1.00 \times 10^5$ | 0 |
| #95001, 0.05 | $8.57 \times 10^{-5}$ | $4.50 \times 10^4$ | 55.0 |
| cisplatin, 0.025 | $8.33 \times 10^{-5}$ | $3.30 \times 10^3$ | 99.0 |
| #95001, 0.025 | $4.29 \times 10^{-5}$ | $9.30 \times 10^4$ | 7.0 |
| cisplatin, 0.012 | $4.00 \times 10^{-5}$ | $1.00 \times 10^4$ | 90.0 |

The methods for treating cancer patients by cis-[Pt($NH_3$)$_2$Cl(Guanosine)]Cl or cis-[Pt($NH_3$)$_2$Pt(Guanosine)$_2$]Cl$_2$ may be described as follow:

cis-[Pt($NH_3$)$_2$Cl(Guanosine)]Cl or cis-[Pt($NH_3$)$_2$(Guanosine)$_2$]Cl$_2$ may be administered to a cancer patient orally or by subcutaneous or intravenous injection, or by means of an implanted reservoir.

cis-[Pt($NH_3$)$_2$Cl(Guanosine)]Cl and cis-[Pt($NH_3$)$_2$(Guanosine)$_2$]Cl$_2$ are slightly soluble in water at room temperature and so injectable compositions are normally in the form of an aqueous solution. If necessary, pharmaceutically-acceptable suspension may be employed. Typically, such a solution or suspension will be employed at a concentration of 1–100 mg/mL more commonly 10–75 mg/mL, for example, 25 mg/mL or 75 mg/mL. The dosage rates by injection are in the range of 5–1,000 mg in the first day of every 1–4 weeks depending upon the patient. Typically, one might administer a dosage of 50–400 mg in the first day of every 1–4 weeks to a patient having a body weight of 40–100 kg, although in appropriate cases such dosages may prove useful for patients having a body weight outside this range. In other cases, dosage as low as 10 mg and as high as 500 mg in the first day of every 1–4 weeks may be appropriate for persons in this body weight range.

cis-[Pt($NH_3$)$_2$PtCl(Guanosine)]Cl or cis-[Pt($NH_3$)$_2$Pt(Guanosine)$_2$]Cl$_2$ may also be administered orally, for example, as a solution or a suspension or as tablets or capsules. Solution and suspension for oral administration are typically of about the same concentration as those used for injection. However, when administering the drug orally, it may be desirable to use a higher dosage rate than when administering it by injection. For example, dosages of 10–1,500 mg in the first day of every 1–4 weeks may be used. Typically, one might administer a dosage of 50–600 mg in the first day of every 1–4 weeks. In preparing such tablets or capsules, standard tablet or capsule making techniques may be employed. If desired, a pharmaceutically acceptable carrier such as starch, mannitol, cellulose or lactose may be used in preparing the tablets or capsules. Capsules may also be prepared using soft gelatin as the encapsulating agent. If desired, such capsules may be in the form of sustained release capsules wherein the main capsule contains microcapsules which release the active ingredient over a period of several hours.

[EXAMPLE 7]

specific formulations which may be used in the treatment of cancer:

(a) Tablets or capsules containing 25, 50 or 100 mg of cis-[$(NH_3)_2$PtCl(Guanosine)]Cl or cis-[$(NH_3)_2$Pt(Guanosine)$_2$]Cl$_2$, (b) Parenteral solution containing 5, 10 or 50 mg/mL, and (c) Liquid formulation for oral administration available in 10, 25 or 50 mg/mL concentration.

These complexes may also be used in the treatment of AIDS. Because of the potential ability of these complexes to hamper the DNA or RNA replication process, it is likely that these complexes are effective against the HIV and may be used for the treatment of AIDS. It may also be used in combination or in tandem with other known AIDS drugs, including but not limited to AZT, to interfere with the HIV enzyme reverse transcriptase and achieve better results.

[EXAMPLE 8]

The methods for treating an AIDS patient by cis-[(NH$_3$)$_2$PtCl(Guanosine)]Cl or cis-[(NH$_3$)$_2$Pt(Guanosine)$_2$]Cl$_2$ may be described as follow:

cis-[(NH$_3$)$_2$PtCl(Guanosine)]Cl or cis-[(NH$_3$)$_2$Pt(Guanosine)$_2$]Cl$_2$ may be administered to an AIDS patient in the same way as in the treatment of a cancer patient. A dosage of 10–600 mg in the first day of every 1–4 weeks may be administered.

When used in conjunction or in tandem with AZT, the dosage of cis-[(NH$_3$)$_2$PtCl(Guanosine)]Cl or cis-[(NH$_3$)$_2$Pt(Guanosine)$_2$]Cl$_2$ may be reduced. A dosage of 5–500 mg in the first day of every 1–4 weeks may be administered with the dosage and the method of administration of AZT maintained the same as its normal usage.

SUMMARY, RAMIFICATION, AND SCOPE

In conclusion, two cisplatin analogs, cis-[Pt(NH$_3$)$_2$Cl(Guanosine)]Cl and cis-[Pt(NH$_3$)$_2$(Guanosine)$_2$]Cl$_2$, may be used for the treatment of cancer and AIDS. The synthesis and the use of these two complexes are presented in this invention.

Although the description above contains many specificities, these should not be construed as limiting the scope of the invention but as merely providing the illustrations of some of the presently preferred embodiments of this invention. For example, the compounds can be made in pure water instead of the mixture of methanol and water.

Thus the scope of this invention should be determined by the appended claims and their legal equivalents, rather than by the examples given.

I claim:

1. A method of treating cancer which comprises administering to a cancer patient a therapeutically effective amount of a complex of the formula cis-[(NH$_3$)$_2$PtGCl]Cl or cis-[(NH$_3$)$_2$PtG$_2$]Cl$_2$, where G is quanosine.

2. A method according to claim 1 wherein the administration is parenteral and a dosage of 5–1,000 mg is administered in the first day of every 1–4 weeks.

3. A method according to claim 1 wherein the administration is parenteral and a dosage of 50–400 mg is administered in the first day of every 1–4 weeks.

4. A method according to claim 1 wherein the administration is oral and a dosage of 10–1,500 mg is administered in the first day of every 1–4 weeks.

5. A method according to claim 1 wherein the administration is oral and a dosage of 50–600 mg is administered in the first day of every 1–4 weeks.

6. The method of claim 1, wherein cancer is breast cancer.

7. A powder form of a complex of the formula cis-[(NH$_3$)$_2$PtGCl]Cl, where G is guanosine.

* * * * *

UNITED STATES PATENT AND TRADEMARK OFFICE
CERTIFICATE OF CORRECTION

PATENT NO. : 5,922,689        Page 1 of 1
DATED : July 13, 1999
INVENTOR(S) : Jiajiu Shaw It is certified that error appears in the above-identified patent and that said Letters Patent is hereby corrected as shown below:

<u>Title page,</u>
ABSTRACT,
Line 2, delete "$(NH_{3)2}$" and substitute -- $(NH_3)_2$ -- in its place.
Line 6, immediately after "treatment" delete "," (comma) and substitute -- ; -- (semicolon) in its place.

<u>Claim 1,</u>
Line 4, delete "quanosine" and substitute -- guanosine -- in its place.

Signed and Sealed this

Fifth Day of March, 2002

Attest:

Attesting Officer

JAMES E. ROGAN
*Director of the United States Patent and Trademark Office*